United States Patent [19]

Witzel et al.

[11] Patent Number: 4,920,959
[45] Date of Patent: May 1, 1990

[54] EXTERNAL FIXTURE FOR OSTEOSYNTHETIS

[75] Inventors: Ulrich Witzel, Wittener Str. 73d, 5600 Wuppertal 2; Karl H. Müller, Bochum, both of Fed. Rep. of Germany

[73] Assignee: Ulrich Witzel, Wuppertal, Fed. Rep. of Germany

[21] Appl. No.: 138,381

[22] PCT Filed: Apr. 6, 1987

[86] PCT No.: PCT/DE87/00146
§ 371 Date: Nov. 20, 1987
§ 102(e) Date: Nov. 20, 1987

[30] Foreign Application Priority Data

Apr. 4, 1986 [DE] Fed. Rep. of Germany ....... 3611319

[51] Int. Cl.$^5$ ............................................. A61B 17/60
[52] U.S. Cl. ......................................... 606/53; 606/96
[58] Field of Search ........... 128/92 Z, 92 ZY, 92 ZK, 128/92 ZW, 92 ZZ

[56] References Cited

U.S. PATENT DOCUMENTS

| | | | |
|---|---|---|---|
| 2,391,693 | 12/1945 | Ettinger | 128/92 Z |
| 2,393,694 | 1/1946 | Kirschner | 128/92 Z |
| 4,475,546 | 10/1984 | Patton | 128/92 ZZ |
| 4,483,334 | 11/1984 | Murray | 128/92 ZW |
| 4,620,533 | 11/1986 | Mears | 128/92 Z |
| 4,693,240 | 9/1987 | Evans | 128/92 ZW |

FOREIGN PATENT DOCUMENTS

| | | | |
|---|---|---|---|
| 140786 | 5/1985 | European Pat. Off. | 128/92 Z |
| 2929455 | 1/1980 | Fed. Rep. of Germany | 128/92 Z |
| 2531332 | 2/1984 | France | 128/92 Z |
| 140329 | 2/1980 | German Democratic Rep. | 128/92 ZW |
| 984468 | 1/1983 | U.S.S.R. | 128/92 ZW |

Primary Examiner—Robert A. Hafer
Assistant Examiner—Kevin G. Rooney
Attorney, Agent, or Firm—Herbert Dubno

[57] ABSTRACT

Any external fixture for bone synthesis is provided with at least one bridge member, a plurality of holders are orientable and screw clampable on this bridge member by clamping surfaces. The holders have cylindrical holder openings which are closable by an operating screw and thereby serve as clamp holders, each for one bone nail and/or one bone screw.

The cylindrical holder openings are bounded by a one piece connected wall surface and are closable individual or jointly with adjacent holder clamp jaw surfaces on the clamp side, on tightening the operating screw. Thus the cylindrical holder openings are each elastically or plastically deformable by a drill and/or screw guide receiving a bone drill with play, from a layer width - down to a smaller width for clamping.

The external fixture affords a simple structure, easy to manufacture and at the same time simple handling during operation.

7 Claims, 10 Drawing Sheets

EXTERNAL FIXTURE FOR OSTEOSYNTHETIS

CROSS REFERENCE TO RELATED APPLICATIONS

This application is a national phase of PCT/DE 87/00146 filed Apr. 6, 1987 and based, in turn, upon German national application No. P 36 11 319.0 of Apr. 4, 1986 under the International Convention.

FIELD OF THE INVENTION

Our present invention relates to an external fixture for osteosynthesis and, more particularly, to a fixture with at least one bridge member on which several holders are orientable and screw-tightenable by means of clamping jaw surfaces, which in turn have cylindrical holder openings closable by operating screws and thereby serve as clamp holders each for one bone nail or screw.

BACKGROUND OF THE INVENTION

The book "Current Concepts of External Fixation of Fractures", by Uhthoff and Stahl, Springer-Verlag, Berlin Heidelberg N.Y., 1982, pp. 99–102 describes earlier fixtures for osteosynthesis.

The previously known external fixture contains two approximately circular cylindrical steel disks of the same circumference traversed coaxially by a common clamp screw. In the space between both clamping disks a thin friction disk can be provided. A clamping disk of the clamping disk pair has two secantial and cylindrical passages extending parallel to each other for receiving the bridge members (fixture frame rods) which penetrate the radial circular surfaces facing the neighboring clamping disk. Two receiving passages longitudinally slotted over a comparatively large peripheral region thus result, in which the fixture frame rods projecting from one side alongside the longitudinal slots must be pushed in axially.

The cylindrical holder openings for receiving either a bone nail (e.g. a Steinmann nail) or a bone screw (e.g. a Schanze screw) are formed in the previously known fixture analogous to the described cylindrical passages for the fixture frame rods as cylindrical passages longitudinally slotted along one side.

Clamping of a fixture frame rod and a bone screw is effected in the known external fixture therefore jointly by tightening the central clamping screw so that both clamping disks are pressed against each other axially with their circular front surfaces facing and, the peripheral portions of the fixture frame rod and the bone screw protruding from the longitudinal slot of the receiving passages are clamped between both.

The external fixtures described by the book "Current Concepts of External Fixation of Fractures", differs significantly from the earlier fixtures and this device offers the advantage of a simple structure including fewer components, however, this device requires improvement with regard to its handling during operation and the subsequent care of the patient.

OBJECT OF THE INVENTION

Departing from the fixture described in the book "Current Concepts of External Fixation of Fractures", it is the object of the invention to improve the heretofore known external fixture operationally, by preserving its advantageously simple structure.

SUMMARY OF THE INVENTION

As opposed to the afore-mentioned known external fixture described in "Current Concepts of External Fixation of Fractures" each cylindrical holder opening consists of a single connected wall surface which is deformable elastically or plastically by operation of a screw element to such an extent that the cylindrical holder opening acts as a drill or screw guide and-after progressively closing and/or constricting it—for clamping a bone nail and/or for the bone screw. According to the invention it is basically possible to close the cylindrical holder opening separately or—analogous to the known fixture—jointly with adjacent clamp jaw surfaces which receive the bridge member (particularly the fixture frame rod).

According to that, the first possibility of such an alternative the cylindrical holder openings are closable on tightening the operating screw by elastic or plastic deformation relative to the bridging member or component first in the sense of an preadjustment and then are deformable with the bone nail and/or with the bone screw with an additional closure stroke from position in which the opening or passage forms a drill and/or screw guide until the passage reaches its final clamped configuration.

In a further embodiment, the second possibility of such an alternative construction, the cylindrical holder openings are closable on tightening the operating screws jointly with the adjacent lateral holder clamp jaw surfaces by elastic or plastic deformation first in the sense of a preadjustment, (with respect to the bridge member) and the cylindrical holder openings then are deformable with the bone nail and/or with the bone screw with an additional closure stroke also closing the clamping surfaces from a drill and/or screw guide position to their final clamped configuration.

A preferred embodiment of the invention, affording particularly advantageous handling in practice, has a cylindrical holder—if necessary jointly with adjacent clamp jaw surfaces—preadjusted by partial closing of the operating screw. This means that the holder on the bridge member (e.g. on a fixture frame rod) is held in place substantially unslidably and the cylindrical holder opening is positioned unadjustably relative to the bridge member and/or in regard to the holder supporting it. For example a bone drill (subsequently, if necessary, a screw tap) can thereby be inserted through the cylindrical holder opening. After removal of the bone drill or tap a bone screw and/or a bone nail (the latter as an implant) can be inserted. As soon as the bone nail and/or the bone screw is mounted through the cylindrical holder opening and is in the bone in its final position, the balance of the closing of the cylindrical holder for clamping can be effected.

From the above disclosure it is apparent that the fixture according to our invention is operationally substantially simpler than earlier devices.

According to the invention an external fixture is particularly advantageous when both the cylindrical holder opening or passage (for successively receiving a drill and a bone screw or a bone nail) and also the clamp jaw surfaces of the associated holder can be operated by a single operating screw and of course brought from the preadjusted configuration to the final clamped configuration. To simplify the operation the operating screw can therefore be a prismatic-head screw provided with manually operable large handling surfaces. An elastic or plastic deformation of the cylindrical holder opening—for example jointly with the adjacent clamp jaw surfaces for the bridge member—is allowed advantageously when the components concerned with the closing are made of a suitable plastic.

Such a plastic can be processed in an injection mold and can contain carbon or glass fiber reinforcement. The use of plastic material—possibly also for the bridge member—gives, aside from a light structure and a simple and economical manufacture, valuable X-ray transparency which does not result with the usual metal external fixtures.

BRIEF DESCRIPTION OF THE DRAWING

In the drawing preferred embodiments of the invention are shown in detail.

SPECIFIC DESCRIPTION

Figure 1:
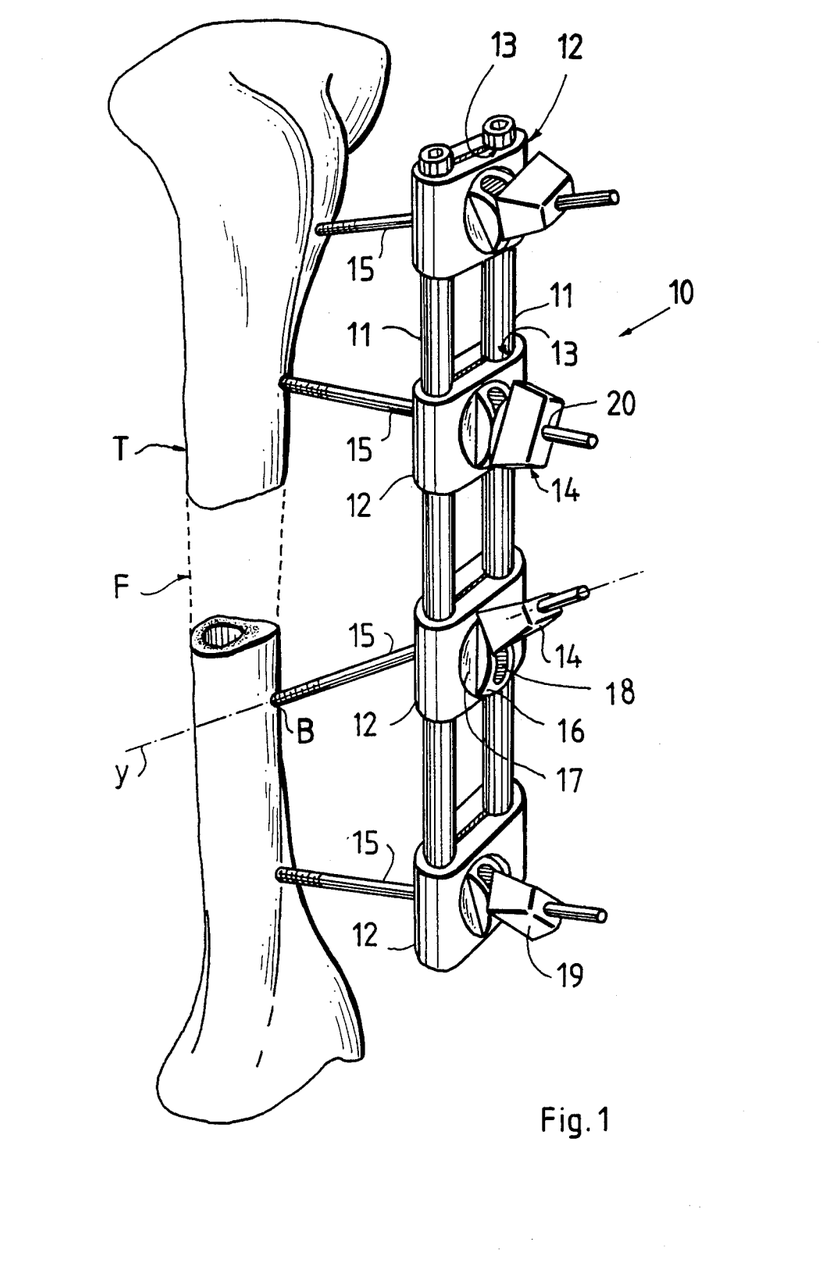
FIG. 1 is a perspective view of an external lateral clamping or monofixture shown connected to the tibia for remote fracture repair.

A complete external fixture 10 according to our invention is shown in FIG. 1. The external fixture is shown in this embodiment with a tibia T in which a remote bone repair is taking place in a fracture region F.

Moreover the fixture 10 has two fixture frame rods 11 which are clamped securely in four holders 12. Each holder 12 is provided with clamping surfaces 13 for receipt of the fixture frame rods 11.

The engagement of the clamping surfaces 13 with the fixture frame rods 11 is caused by operating screws 14. By tightening the operating screws 14 cylindrical holder openings not seen in FIG. 1 are closed to secure the bone screw 15 (e.g. so-called S change screws) received in each of them.

Figure 15:
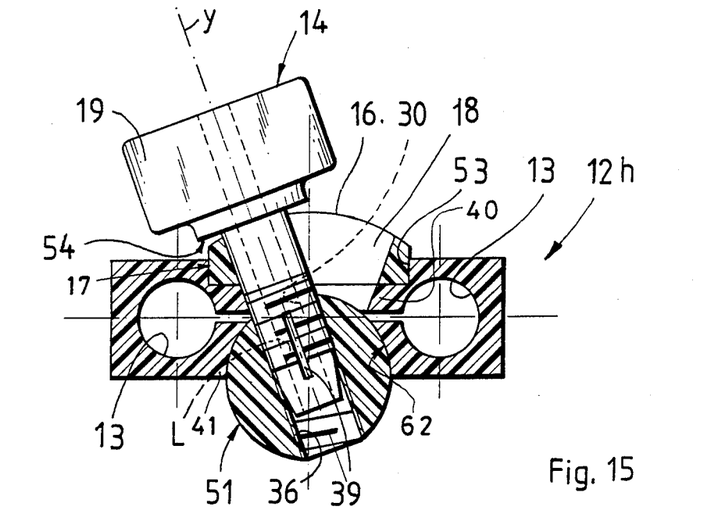
FIGS. 15 and 16 shows additional embodiments of the clamp members of our invention analogous to that according to FIG. 14 and in corresponding cross sectional views.
Figure 16:
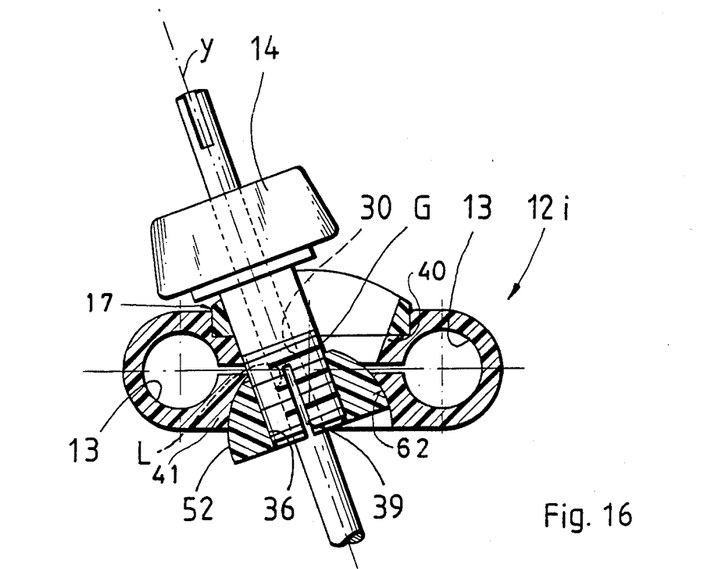
Figure 17:
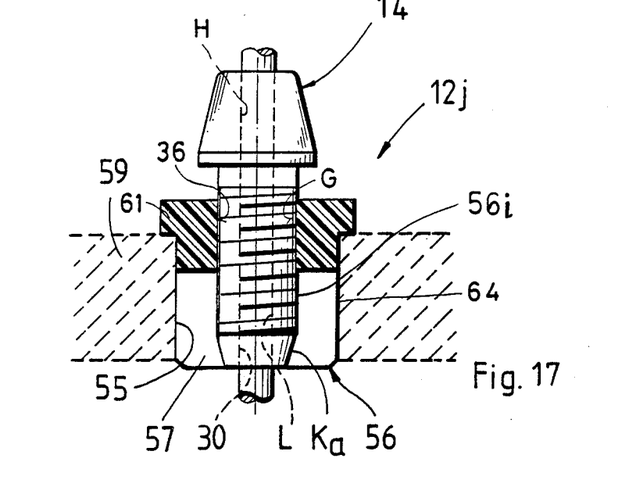
FIGS. 17 to 20 are sectional views which show plug like holders used with substantially plate and/or honeycombed like bridge members.
Figure 18:
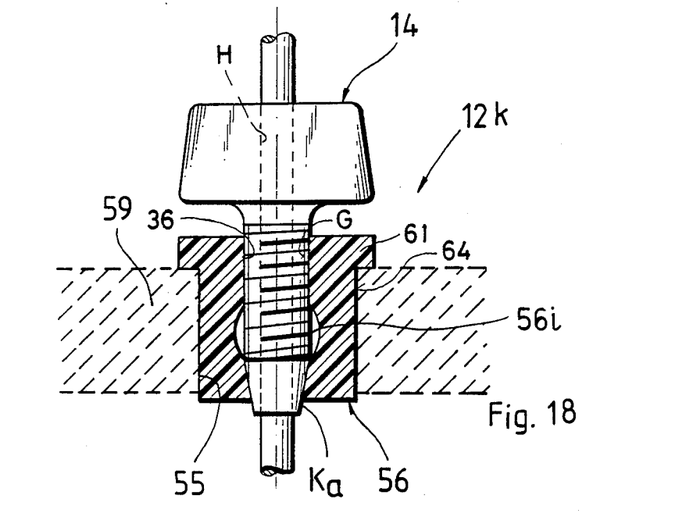

Components for receiving the bone screws 15 are provided as shown in FIGS. 15 and 16. Washers 17 which assist in the spatial orientation of the bone screws 15 are part of these components. The rotatable washers 17 are each provided with an elongated hole 18 in the vicinity of its spherical surface 16 for receipt of the screw shaft of the operating screw 14 which can recline the bone screw 15.

The practical manipulation of the external fixture shown in FIG. 1 is as follows:

The relative positioning of the holder 12 on the bridge member (fixture frame rods 11) is caused by partially tightening the related operating screw 14 with its operating lever 19. Moreover the longitudinal axis y of each operating screw 14 is secured in the desired spatial position by this partial tightening.

A bone drill is then axially fed through the front opening 20 (which extends into the cylindrical holder) of the associated operating screw 14 and the bone drill B is introduced into the tibia T. A screw tap is inserted through the opening 20 of the operating screw 14 after removal of the bone drill and provides the bone hole B with an interior thread. The bone screw 15 is inserted through the opening 20 of the operating screw 14 after withdrawing the bone-tap drill. After the bone screw 15 has reached its final attachment position in the threaded bone hole B the associated operating screw is tightened manually by operating screw handle 19. Because of that both the holder 12 on the associated fixture frame rods 11, the bone screw 15 inside the operating screw 14 and also finally the pivot system (of which only the washer 17 is shown in FIG. 1) are fixed rigidly in position relative to the fixture frame rod 11.

With the aid of the arrangement according to FIG. 1, it can be easily imagined that the structural components shown there can also be used for installation of a fixture frame or a fixture framework. Thus additional holders 12 (not shown) are clamped on one end on both fixture frame rods 11 and act as coupling members for respective laterally adjacent fixture frame rods 11. In this way holders 12 (with operating screws 14) for holding Steinmann nails are positioned diametrically opposing each other on opposite sides of the tibia T. The use of the fixture 10, if desirable also pivotally mounted, is understandably not limited to a tibia T but advantageously also to other extremities and to the pelvis.

Figure 2:
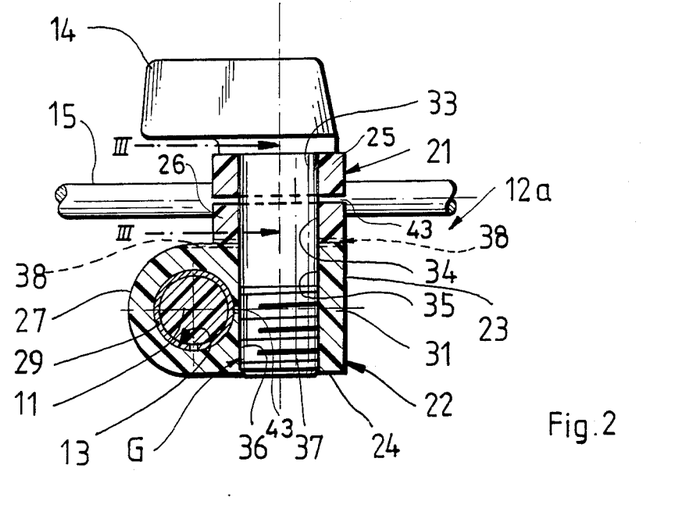
FIG. 2 is a cross sectional view of a two member holder of the external fixture one member of which receives a bone screw and whose other member receives a fixture frame rod.
Figure 3:
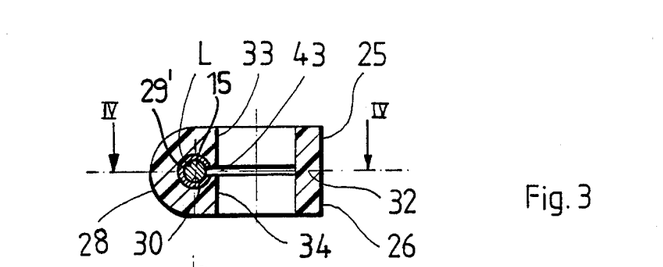
FIG. 3 is a cross sectional view taken along the section line III—III of FIG. 2.
Figure 4:
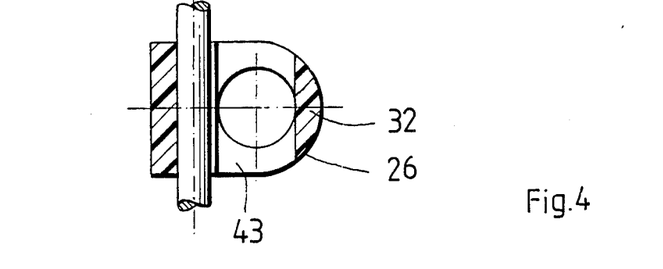
FIG. 4 is a cross sectional view taken along the section line IV—IV in FIG. 3.

In the embodiment of our invention according to FIGS. 2-4 the twin holders 12 have two clamp members 21 and 22.

Each clamp member 21, 22 has two clamping arms 23, 24 and 25, 26 respectively parallel to each other. The two clamping arms 23, 24 and/or 25, 26 are attached to one another by a slotted tube section 27, 28.

The slotted tube section 27 of the clamp member 22 forms the clamp jaw surface 13 for the fixture frame rod 11 made of carbon fiber reinforced plastic material. For the case in which fixture frame rods 11 with diameter variations are used a fitting sleeve 29 is inserted on the clamp jaw surface 13 for compensation of undersize fixture frame rods. The fitting sleeve 29 thus forms a circumferentially variable fitting sleeve.

The other clamp member 21 contains the cylindrical holder opening 30 for receiving the bone screw 15.

A feature of both clamp members 21 and 22 having only one slotted tube section 27 and/or 28 on one end is that their clamping arms 23, 24; 25, 26 are connected with each other in one piece by connecting bridges 31, 32 respectively. The connecting bridges 31, 32 result in definite clamping characteristics.

Of the four successively positioned clamping arms 23, 24; 25, 26 three clamping arms 25, 26 and 23 each have smooth interior passages 33, 34, 35 and the remaining clamping arm 24 has an interiorly threaded passage 36 for the threaded part 37 of the common operating screw 14 which does not by itself form the cylindrical holder opening 30 according to FIGS. 2–4.

Both the clamp jaw surfaces 13 and the cylindrical holder passage 30 are jointly operated by the operating screw 14 in the embodiment according to FIGS. 2 to 4. As has already been illustrated in conjunction with FIG. 1 the securing of the holder 12 relative to the fixture frame rods 11 and the bone screw 15 and/or in regard to an unshown drill is possible. First an additional tightening of the operating screw 14 causes a common final clamping of the fixture frame rod 11 in regard to the clamp jaw surface 13 and/or in regard to the slotted sleeve 29 and of the bone screw 15 in regard to the cylindrical holder opening 30.

To secure the relative rotational position of the clamp members 21, 22 to each other planar grooved serrations 38, i.e. so-called "Hirth serrations", are provided on the contacting surfaces facing each other.

Figure 5:
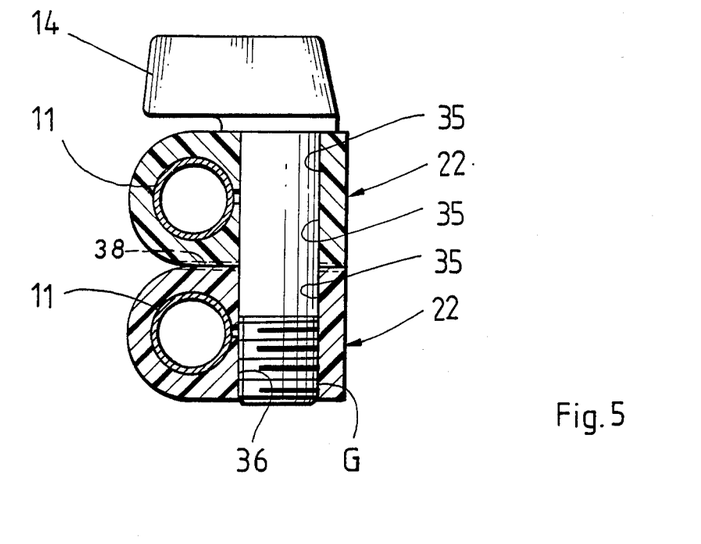
FIG. 5 is a view similar to FIG. 2 which shows an embodiment in which two fixture frame rods cooperate.
Figure 6:
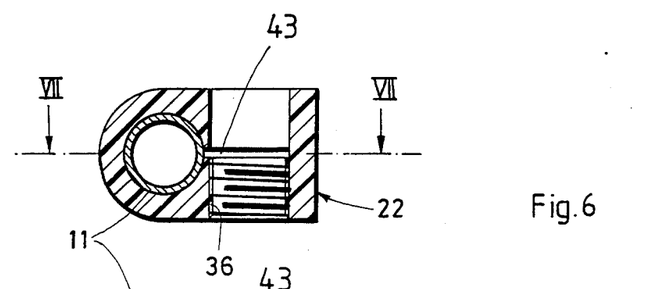
FIG. 6 is a detail sectional view through the lower clamp member of the device of FIG. 5 without the operating screw and without the fixture frame rod.
Figure 7:
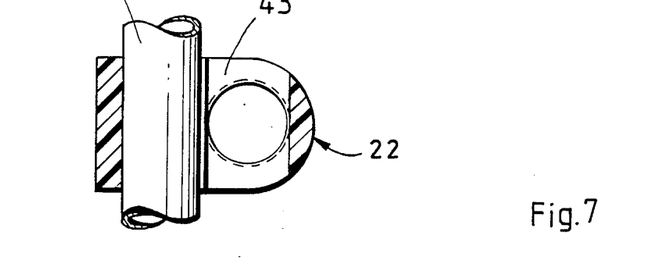
FIG. 7 is a cross sectional view taken along the section line VII—VII in FIG. 6.

In the embodiment of FIGS. 5–7 two substantially identical clamp members 22, 22 are provided each having a smooth passage 35 while the lower of the two clamp members has an interior threaded passage 36. The clamping of both clamp members 22, 22 which each receive a tube like fixture frame rod 11 occurs analogous to the clamping occurring in the embodiment provided in FIGS. 2–4. A cylindrical holder opening 30 is not shown in the embodiment of FIGS. 5–7, because the operating screw 14 contains a cylindrical holder opening 30, substantially similar to the operating screw 14 according to FIG. 8.

Figure 8:
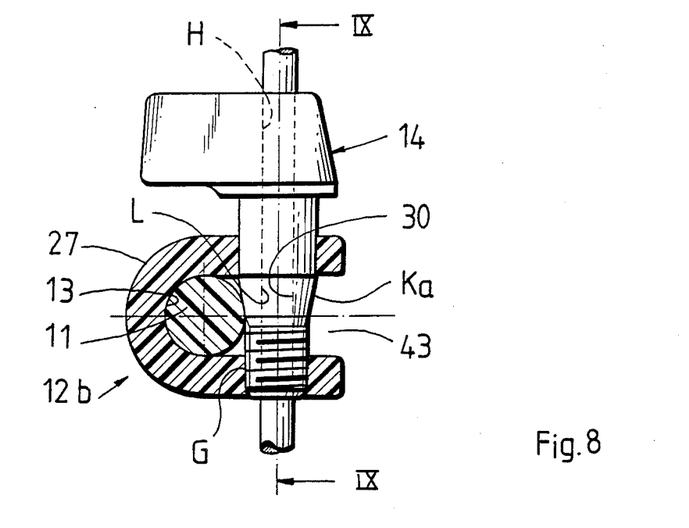
FIG. 8 is another view similar to FIG. 2 but which shows another embodiment provided with a clamp member in which both a bone nail and a fixture frame rod can be secured directly by a single operating screw.
Figure 9:
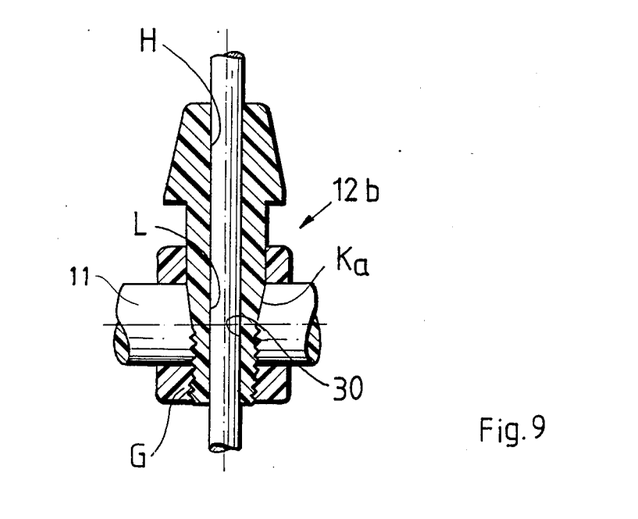
FIG. 9 is a cross sectional view taken along the section line IX—IX in FIG. 8.

In the embodiment of FIGS. 8 and 9 the operating screw 14 is traversed by an axial passage H which contains the wall surface L forming the cylindrical holder opening 30. Above the outer threaded portion G of the operating screw 14 there is an exterior cone $K_a$. This outer cone $K_a$ is located substantially upwardly from the threaded portion G on the axis of the cylindrical holder opening 30. When the operating screw 14 is tightened, the outer cone $K_a$ contacts increasingly on the outer surface of the fixture frame rod 11 whereby the outer surface of the fixture frame rod 11 is pushed against the clamping surface 13 of the slotted tube section 27. On the interior of the outer cone $K_a$ alone—and thus the wall surface L—is deformed elastically in the sense of a narrowing. It remains to be noted that the operating screw 14 and the clamp member holder 12b (like the similar components in the foregoing and following FIGURES) are made from an entropically elastically deformable plastic and of course as an injection molded components. A plastic material including fiber components, especially carbon and glass fibers, is used.

In the embodiments of FIGS. 10–13 the operating screw 14 has the holders 12c, 12d, 12e and 12f with essentially the same structure. The outer cone $K_a$ of the operating screw 14 is provided with at least two clamping slots 39 which should easily allow a narrowing of the cylindrical holder opening 30 with the wall surface L on tightening the operating screw 14.

As a resistive surface and/or stop member for the outer cone $K_a$ the upper clamp member 23 and/or 40 has a conical opening $K_i$ (inner cone) correlated to the outer cone $K_a$. The lower clamp member 24 and/or 41 is provided with the inner thread 36 for receiving the outer thread G. Hence the clamp members 23, 24; 40, 41 (with their clamping surfaces 13) are simultaneously closed on the cylindrical holder openings.

Figure 10:
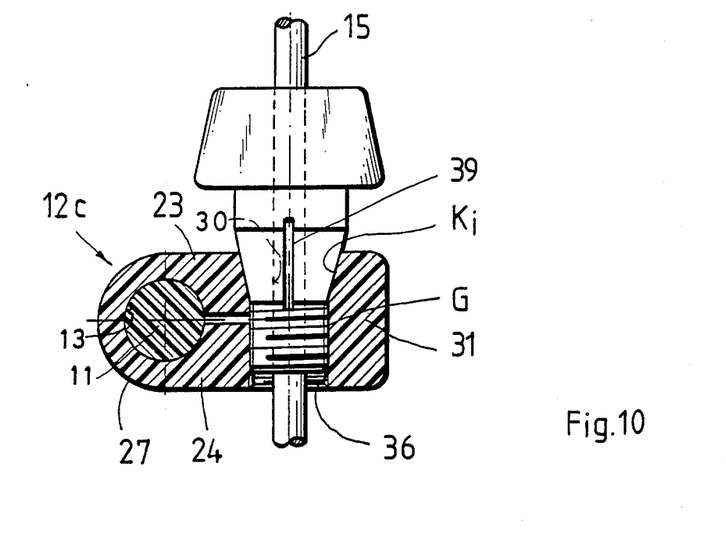
FIG. 10 shows a simple clamp member in a view analogous to the representation in FIG. 8 in which however the clamping of the fixture frame rod occurs indirectly.
Figure 11:
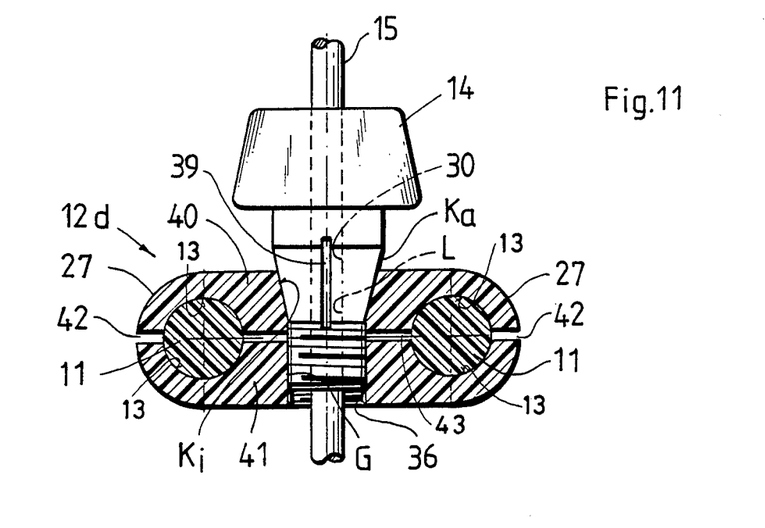
FIG. 11 is a cross sectional view which shows a holder with two clamp members which is approximately the twin of the unit shown in FIG. 10.
Figure 12:
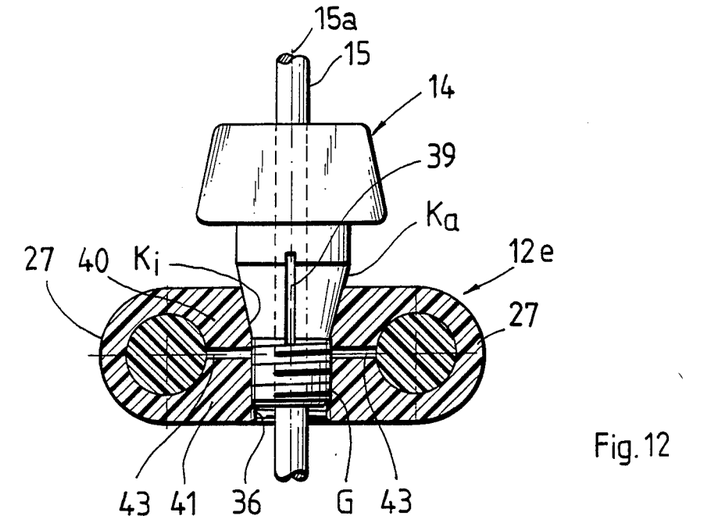
FIG. 12 is a view similar to that of FIG. 11 in which both clamp jaw regions of twin clamp members are slotted.

The embodiment shown in FIGS. 11–12 is different only in so far as FIGS. 11 and 12 show a twin clamp member arrangement for receipt of two fixture frame rods 11 while only a single clamp member 12d is shown in FIG. 10. The embodiment of FIG. 11 has on the contrary a slotted tube section longitudinally divided by axial slots 42 so that in this case two approximately shell shape clamping components with the clamping arms 40, 41 and the divided slot tube region 27 result.

In the embodiment of FIG. 10 only the simple member or clip 12d with the undivided slotted tube section 27 and a connecting bridge 31 between both clamp members 23, 24 is provided.

Figure 13:
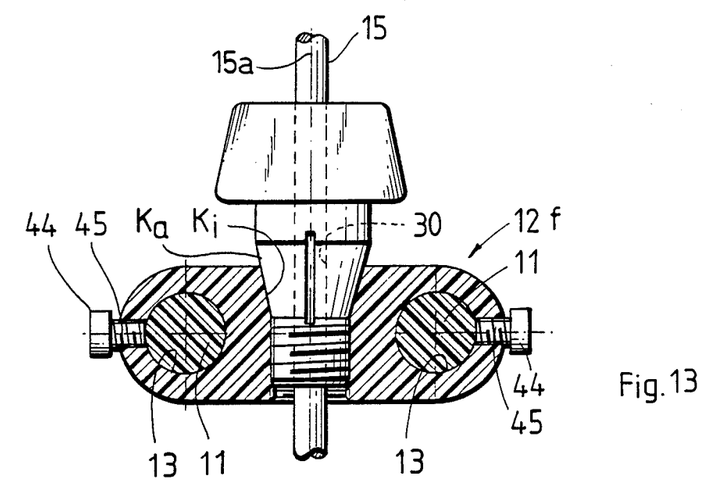
FIG. 13 is another cross section which shows an embodiment similar to FIG. 12 in which a securing of the holder to the fixture frame rod which is separate from the securing of the bone screw (inside of the operating screw) is possible.

The embodiment of FIG. 13 differs from that of FIG. 12 only in that it has no slot 43 to define a slotted tube section 27. Furthermore the holder component 12f forms clamp jaw openings 13 which provide a securing of the fixture frame rods 11 by, for embodiment, specially threaded pins 45 provided with a clamp handle or knob 44. The clamping of the bone screw 15 inside of the cylindrical opening occurs by the press-cone arrangement $K_a$ and $K_i$ similar to the embodiment of FIG. 12.

Figure 14:
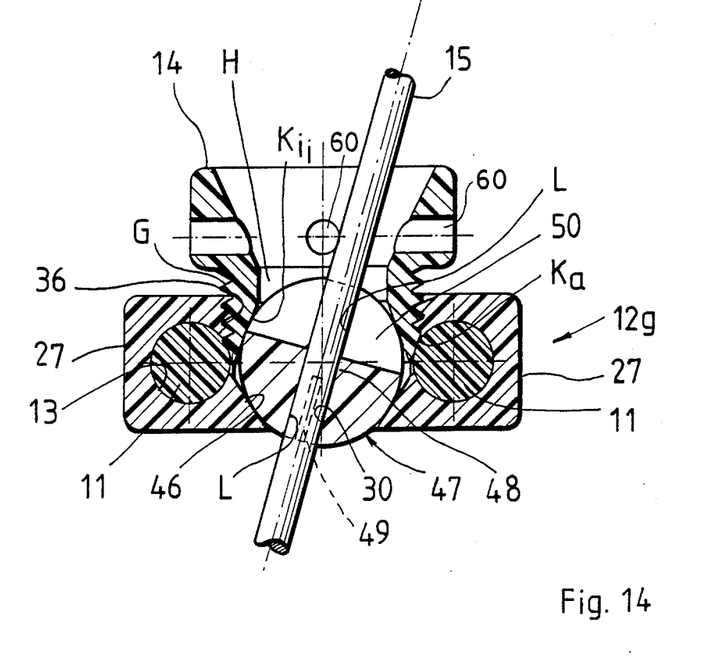
FIG. 14 is a similar view which shows an embodiment with twin clamp members analogous to FIG. 12 with space pivotal positioning and securing of a bone screw and the advantage of a direct securing of both fixture frame rods by the operating screw.

The embodiment of FIG. 14 with the holder 12g forms a variation of the embodiment of FIG. 12, however with the advantage of a space pivot orientability and securing the cylindrical holder opening 30 with its wall surface L. The advantage of a simultaneous direct clamping of both fixture frame rods 11 by the operating screw 14 is obtained. Of course a holder-side spherical ball socket 46 is provided in the holder 12g in which a clamping ball 47 is space pivotally mounted. The clamping ball 47 made of a suitable plastic material has a radially running lower slot 49 and a slotted hole, slot or cavity 50 facilitating displacement approximately 90° with a solid intermediate material between them. The clamp slots or cavities 49, 50 should make the closability in the vicinity of the wall surface of the cylindrical holder opening 30 easier. This closability occurs in this embodiment of FIG. 14 as follows:

The operating screw 14 provided with an axial hollow space H has an inner cone $K_{ii}$ on its free end which presses from the outside against the clamping ball 47 while the operating screw 14 is tightened. On the free end of the outer thread G of the operating screw 14 an outer cone $K_a$ is found which presses against the outer surface of the fixture frame rods 11. In this way in the embodiment of FIG. 14 a clamping of the bone screw 15—also in the sense of a preadjustment—inside of the cylindrical holder opening 30 and also a holding of the fixture frame rods in place occurs inside of the clamp jaw surfaces 13.

The screw head of the operating screw 14 is provided with an insertion opening 60 for the tool to be inserted.

In FIGS. 15 and 16 the holders $12_h$ and $12_i$ related structurally to each other are shown.

Also in the embodiments of FIGS. 15 and 16 the screw axis y is pivotally orientable in space, i.e. can be swiveled, and fixable. The here-provided clamping ball 51 (FIG. 15) or the clamping ball 52 (FIG. 16) can be formed as threaded members. The specially threaded members 51, 52 are provided with an interior thread 36 for receipt of the exteriorly threaded member G of the operating screw 14. So that a narrowing of the cylindrical holder opening 30 with the operating screw 14 receiving the wall surface L can occur the threaded portion G has a clamping slot 39 in the axial longitudinal portion of the wall surface L. For the case in which greater clamping force must be applied the ball 51 is provided while a hemispherical ball 52 suffices for lower clamping force (small axial length of the threads 36).

For receiving the ball 51 resp. the hemispherical ball 52 each clamp member 41 is provided with a spherical ball socket 62.

The washer 17 already mentioned in connection with FIG. 1 with their spherical surface 16 is shown in detail in FIGS. 15 and 16. The washer 17 has a circular cylindrical basic form and is positioned rotatably in a circular cylindrical recess 53. For pivotability of the shaft of the screw 14 the elongated hole (pivot opening) 18 is provided. The spherical surface 16 forms therefore the bearing surface for the lower side of the screw head 19. Also in the embodiment of FIGS. 15 and 16 a combined adjustment—also in the sense of a preadjustment—of the cylindrical holder opening 30 of the threaded members 51 resp. 52 and the unshown fixture frame rods 11 inside the clamp jaw surfaces 13 is possible.

FIGS. 17–20 show a stopperlike insert 61 provided with contacting surfaces in the holders $12j$–$12m$ for each receiving opening 55 (not shown in FIGS. 19 and 20) of a plate like and/or honeycomb like bridge member 59 made of a plastic transparent to X-ray radiation.

Each stopperlike insert $12j$–$12m$ with inner threads 36 forms a spreading body 56 with outer clamp jaw surfaces 64 which is pressed against the wall of the receiving opening 55 on tightening the operating screw 14, preferably, facilitated by the clamping slot 57. Thus the operating screw 14 with the threaded section G is provided with an outer cone $K_a$ of FIG. 17 which moreover causes a deformation of the cylindrical holder opening 30 with its wall L. The same principle is followed in the embodiment of FIG. 18.

Figure 19:
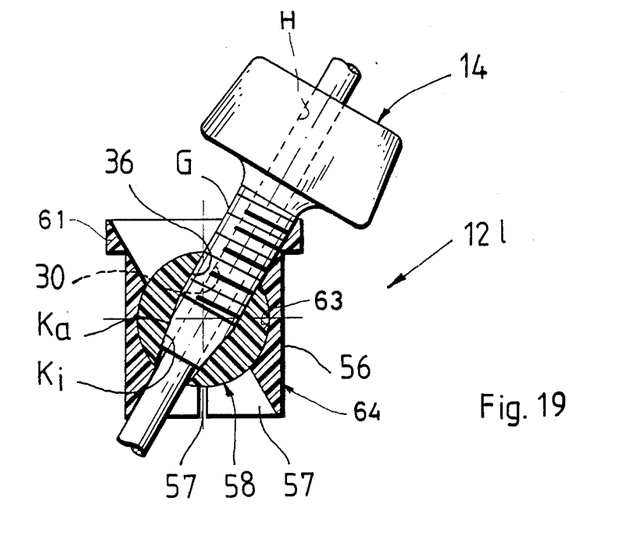

As can be seen from FIG. 19 a roller like threaded member 58 is provided with an inner thread 36 for the outer thread member G of the operating screw 14 inside of a circular cylindrical bearing socket 63 of the insert $12l$. The roller 58 has an inner cone $K_i$ against which the outer cone $K_a$ of the operating screw 14 contacts causing both the elastic deformation of the clamping roller 58, a narrowing of the cylindrical holder opening 30 and a spreading of the spreading body 56.

Figure 20:
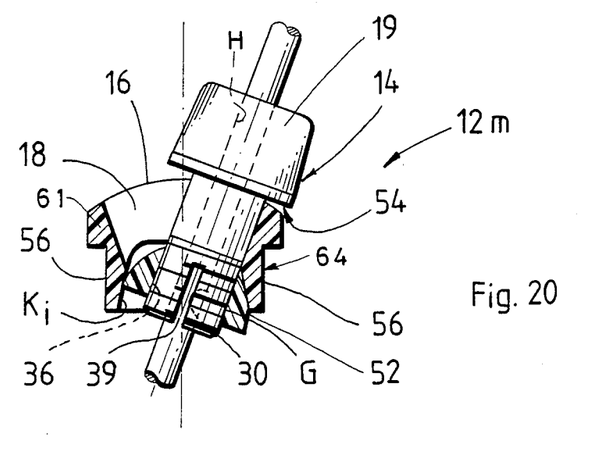

In the embodiment of FIG. 20 the holder $12m$ formed as a special threaded member has a hemispherical clamping ball 52 with the inner thread 36 for the outer thread G of the operating screw 14 which can contact against the inner surface of the elastically deformed spreading body 56 which forms an inner cone $K_i$ of the components closing it. Similar to the embodiment of FIGS. 15 and 16 an elongated hole like pivot opening 18 of the upper portion of the component supporting the spreading body 56 has an elongated pivot opening 18 which is enclosed by a spherical surface 16 as a bearing surface for the underside 54 of the screw head 19. Also the threaded member G is provided in the axial longitudinal region of the cylindrical holder opening 30 with a clamping slot 39.

In all stopperlike embodiments of FIGS. 17–20 the movability of the components 58, 59 is or completed by the rotatability of the insert $12l$, $12m$ in the cylindrical receptacle 55 of the honeycomb and/or plate like bridge member 59 complementing the space pivotability.

We claim:

1. An external fixture for securing bone parts for osteosynthesis, comprising:
    a support having two spaced-apart parallel rods;
    a plurality of holders secured to said rods, each of said holders comprising:
    clamping means formed by a one-piece body constituting a sleeve having a slit defining two juxtaposed clamping surfaces flanking said rods from opposite sides thereof and on opposite sides of said sleeve and formed with respective generally cylindrically segmental cavities receiving the respective rods whereby said rods are clamped between said clamping surfaces, when said members are drawn toward one another, said clamping surfaces on opposite sides of the sleeve being formed with mutually registering holes,
    an operating screw having a head engageable by a user to rotate said screw and a screwthread, said screw passing through said holes and being rotatable to draw said clamping surfaces toward one another and clamp said clamping surfaces against said rods, said operating screw being formed with an axial bore adapted to constrict upon tightening of said screw,
    an internally threaded member engaging the screwthread of said operating screw at an end thereof opposite said head, and
    means including said internally threaded member forming a swivel enabling said screw to swing relative to said body in said holes and locking said swivel into a fixed position in said body upon tightening of said screw into said member; and
    a respective bone screw or bone nail passing through and received in a respective one of said axial bores in a respective operating screw, clamped in the respective bore upon tightening of the respective operating screw into the respective member and fixed in a respective one of said bone parts at an angular orientation determined by an angle at which the respective swivel is locked in the respective body.

2. The external fixture defined in claim 1 wherein said sleeve is slotted along one side thereof.

3. The external fixture defined in claim 1 wherein said member is received in one of said holes and said swivel further includes a washer having a slot through which said operating screw passes and received rotatably in the other of said holes.

4. The external fixture defined in claim 3 wherein said washer has a spherical surface against which said head bears upon tightening of said screw.

5. The external fixture defined in claim 3 wherein said one of said holes has a generally spherical cavity and said member swivels therein.

6. The external fixture defined in claim 5 wherein said member has a spherical surface received in said cavity.

7. The external fixture defined in claim 1 wherein said body and said operating screw of each of said holders is composed of injection-molded synthetic resin.

* * * * *